(12) United States Patent
Pohlmeier et al.

(10) Patent No.: US 9,592,329 B2
(45) Date of Patent: Mar. 14, 2017

(54) SYSTEM FOR CARRYING OUT A BLOOD TREATMENT

(75) Inventors: Robert Pohlmeier, Bad Homburg (DE); Michael Herrenbauer, Neu-Anspach (DE); Patricia Goempel-Klein, Wehrheim (DE); Alfred Krause, Wehrheim (DE); Wolfgang Wehmeyer, Tuebingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 477 days.

(21) Appl. No.: 13/634,355

(22) PCT Filed: Mar. 14, 2011

(86) PCT No.: PCT/EP2011/001261
§ 371 (c)(1),
(2), (4) Date: Sep. 12, 2012

(87) PCT Pub. No.: WO2011/113572
PCT Pub. Date: Sep. 22, 2011

(65) Prior Publication Data
US 2013/0001165 A1    Jan. 3, 2013

(30) Foreign Application Priority Data
Mar. 15, 2010  (DE) .................. 10 2010 011 465

(51) Int. Cl.
*A61M 1/16*    (2006.01)
(52) U.S. Cl.
CPC ..... *A61M 1/1656* (2013.01); *A61M 2209/084* (2013.01); *A61M 2209/088* (2013.01)

(58) Field of Classification Search
CPC .......... A61M 1/1656; A61M 2209/084; A61M 2209/086
(Continued)

(56) References Cited

U.S. PATENT DOCUMENTS 4,229,299 A    10/1980   Savitz et al.
4,765,888 A    8/1988    Barthe et al.
(Continued)

FOREIGN PATENT DOCUMENTS

| AU | 4017885 | 9/1985 |
|----|---------|--------|
| CN | 1859936 | 11/2006 |

(Continued)

OTHER PUBLICATIONS

Drukker et al."Replacement of Renal Function by Dialysis", Hemodialysis Machines and Monitors, 1996, ISBN 0-7923-3610-0, S. 342-343.
(Continued)

*Primary Examiner* — John Kim
(74) *Attorney, Agent, or Firm* — Jacobson Holman, PLLC.

(57) ABSTRACT

The present invention relates to a system for the carrying out of a blood treatment, in particular a dialysis treatment, wherein the system has at least one blood treatment device, in particular a dialyzer, and at least one tank from which treatment fluid, in particular dialysis fluid, is removed during the carrying out of the blood treatment and/or into which consumed treatment fluid, in particular consumed dialysis fluid, is filled during the carrying out of the blood treatment, wherein the tank is an element of at least one mobile apparatus which can be connected to the blood treatment device such that at least one fluid connection can be established between the tank and the blood treatment device.

15 Claims, 2 Drawing Sheets

(58) Field of Classification Search
USPC ............ 210/645, 646, 198.1, 232, 235, 236, 210/257.1, 261, 321.71
See application file for complete search history.

(56) References Cited

U.S. PATENT DOCUMENTS

| | | | |
|---|---|---|---|
| 5,914,047 | A | 6/1999 | Griffiths |
| 8,317,099 | B2 | 11/2012 | Perkins et al. |
| 8,671,996 | B2 | 3/2014 | Weilhoefer et al. |
| 2001/0044731 | A1 | 11/2001 | Coffmann et al. |
| 2002/0023879 | A1 | 2/2002 | Hadden |
| 2003/0085684 | A1 | 5/2003 | Tsukamoto et al. |
| 2004/0176984 | A1 | 9/2004 | White et al. |
| 2005/0187529 | A1 | 8/2005 | Reasoner et al. |
| 2007/0060871 | A1 | 3/2007 | Istoc et al. |
| 2007/0135779 | A1 | 6/2007 | Lalomia et al. |
| 2008/0300658 | A1 | 12/2008 | Meskens |
| 2009/0012448 | A1 | 1/2009 | Childers et al. |
| 2009/0069784 | A1 | 3/2009 | Estes et al. |
| 2009/0322545 | A1* | 12/2009 | Gibson ............. A61M 5/14546 340/618 |
| 2010/0078092 | A1 | 4/2010 | Weilhoefer et al. |
| 2010/0093401 | A1 | 4/2010 | Moran |
| 2010/0137782 | A1 | 6/2010 | Jansson et al. |
| 2010/0204765 | A1 | 8/2010 | Hall et al. |
| 2011/0196279 | A1 | 8/2011 | Maiefhofer et al. |
| 2013/0001165 | A1 | 1/2013 | Pohlmeier et al. |

FOREIGN PATENT DOCUMENTS

| | | |
|---|---|---|
| CN | 101622021 | 1/2010 |
| CN | 1027891305 | 11/2012 |
| DE | 1 939 923 | 5/1970 |
| DE | 93 02 790 | 6/1994 |
| DE | 19825158 C1 * | 4/1999 |
| DE | 10 2007 009269 | 8/2008 |
| DE | 102008050849 | 4/2010 |
| EP | 1543853 | 6/2005 |
| JP | H1085322 | 4/1998 |
| JP | 2002536126 | 10/2002 |
| JP | 2008535569 | 9/2008 |
| WO | WO 99/00154 | 1/1999 |
| WO | WO 01/64262 | 9/2001 |
| WO | WO 2004/062710 | 7/2004 |
| WO | WO 2006/108026 | 10/2006 |
| WO | WO 2007/048068 | 4/2007 |
| WO | WO 2008/082033 | 7/2008 |
| WO | WO 2008/104367 | 9/2008 |

OTHER PUBLICATIONS

Armin Gärtner, "Medizinishce Netzerke und vernetzte medizinische Systeme—Teil 1", S. 169-173, Medizintechnik 129 (2009) Nr. 5, ISSN 0344-9416. (English abstract included).

Armin Gärtner, "Medizinishe Netzwerke und vernetzte medizinische Systeme—Teil 2", Medizintechnik 129 (2009) Nr. 6, S. 213-217, ISSN 0344-9416. (English abstract included).

Armin Gärtner, "Medizinishce Netzwerke Teil 3: Virtualisierung und shared network," Medizintechnik 130 (2010) NR. 1, S. 13-19, ISSN 0344-9416. (English abstract included).

Armin Gärtner, Funktrasponder 9RFID-Technologie) in der Medizintechnik, Medizintechnik 126 (2006) Nr. 4, S. 136-145, ISSN 0344-9416 (English abstract included).

* cited by examiner

SYSTEM FOR CARRYING OUT A BLOOD TREATMENT

This is a national stage of PCT/EP11/001261 filed Mar. 14, 2011 and published in German, which has a priority of German no. 10 2010 011 465.0 filed Mar. 15, 2010, hereby incorporated by reference.

The present invention relates to a system for the carrying out of a blood treatment, in particular of a dialysis treatment, wherein the system includes at least one blood treatment device, in particular a dialyzer.

Dialyzers are known from the prior art in which the dialysis fluid is not manufactured during a treatment, but in which rather the total amount of dialysis fluid required for a dialysis treatment is provided in a tank prior to the treatment. Dialyzers of this type are also called "batch-type" dialyzers.

It is furthermore known from the prior art in accordance with WO 2008/104357 A2 to connect these devices to a mobile unit in which the dialysis fluid is prepared and from which the prepared dialysis fluid is filled into the tank of the dialyzer.

In the system known from WO 2008/104367 A2, the prepared dialysis fluid is thus transferred from the tank of the mobile unit into the tank of the dialyzer.

It is the underlying object of the invention to further develop a system of the initially named kind such that the system is simple to handle and enables a change of the treatment fluid while the patient remains connected to the treatment unit of the system.

This object is solved by a system having the features for the carrying out of a blood treatment, in particular a dialysis treatment, wherein the system has at least one blood treatment device (100), in particular a dialyzer (100), and at least one tank (210) from which treatment fluid (220), in particular dialysis fluid (220), is removed during the carrying out of the blood treatment and/or into which consumed treatment fluid (230), in particular consumed dialysis fluid (230), is filled during the carrying out of the blood treatment, wherein the tank (210) is an element of at least one mobile apparatus (200) which can be connected to the blood treatment device (100) such that at least one fluid connection can be established between the tank (210) and the blood treatment device (100). Provision is accordingly made that the tank from which treatment fluid, in particular dialysis fluid, is removed during the blood treatment is an element of at least one mobile apparatus which can be connected to the blood treatment device such that at least one fluid connection can be established between the tank and the blood treatment device. Provision is thus made in accordance with presently claimed invention that the tank from which the dialysis fluid is removed during the blood treatment or dialysis treatment is an element of a mobile device, that is, of a device which can be moved by a user and which is connected to the blood treatment device before the treatment such that a fluid connection is made between the tank and the blood treatment device so that the treatment fluid can be supplied to the blood treatment device.

It is conceivable that the blood treatment device itself does not have any tank from which treatment fluid, in particular dialysis fluid, is removed during the blood treatment and/or into which consumed treatment fluid, in particular consumed dialysis fluid, is filled during the carrying out of the blood treatment.

In such an embodiment of the invention, it is, however, not precluded that, for example, one or more containers for anticoagulants or other additives are arranged at the blood treatment device itself.

An embodiment is also conceivable and is covered by the invention in which a comparatively small buffer store, for example a container with a volume of up to 1 l, is arranged at the blood treatment device itself. This, for example, allows the blood return while no batch is connected.

The blood treatment device itself can thus be made comparatively simple since it does not have its own tank which serves the reception of dialysis fluid in this case. The advantage of this embodiment lies in the flexibility and in the possibility of a tank change.

In a further embodiment of the invention, the system has means which are made such that they establish at least one fluid connection between the tank and the blood treatment device automatically or on demand after the moving of the mobile apparatus into a predetermined position into the blood treatment device.

It is generally conceivable that the blood treatment device automatically recognizes the presence of the mobile apparatus and then establishes at least one fluid connection between the tank and the blood treatment device either automatically or on demand by the user so that the dialysis fluid can be supplied to the blood treatment device or to its means for the carrying out of a blood treatment.

Means can be provided for the establishment of a fluid connection between the tank of the mobile apparatus, on the one hand, and the blood treatment device, on the other hand. They can include hoses and/or connection elements through which the treatment fluid flows after the connection. The named means can be arranged in or at the blood treatment device and/or in or at the mobile apparatus.

It is generally conceivable that the blood treatment device automatically recognizes when the mobile apparatus has been moved into a predetermined and designated end position and then automatically establishes a fluid connection and/or a data connection or at least gives the user the option of establishing corresponding connections on demand.

If it is a case of a fluid connection, it is to be made such that the risk of microbial contamination (in accordance with the prior art) is minimized, with the fluid connection been established, for example, by corresponding connection elements between the at least one tank, on the one hand, and the blood treatment device, on the other hand.

Provision is made in another embodiment of the invention that the blood treatment device has a mount, preferably a cut-out or a space, for the reception of the mobile apparatus. To be able to start a dialysis treatment, the mobile apparatus is introduced into this cut-out or into the space provided for it and is connected. The blood treatment can subsequently be started by the blood treatment device or by its means for the carrying out of an external blood treatment.

It is of advantage for the secure integration of the mobile apparatus in the blood treatment device that the mobile apparatus is easy to maneuver and is connected, preferably latched, to the blood treatment device in a suitable manner. The good maneuverability of the mobile apparatus can be achieved, for example, by casters of the mobile apparatus or by a suitable caster system. The casters or the caster system are preferably made such that a reliable directional stability of the mobile apparatus is ensured since the mobile apparatus must preferably be pushed into the blood treatment device with directional stability.

The caster system or the casters should at the same time be made such that a comparatively simple steerability of the mobile apparatus is ensured. It can have a weight in the filled state in the order of magnitude of approximately 15 kg to 150 kg, in particular less than 120 kg and, for example, 80 kg.

Provision is furthermore made in a preferred embodiment of the invention that the casters of the mobile apparatus project as little as possible to the side or take up a "track width" which is as small as possible, are designed as flat and as not moving outwardly where possible or moving outwardly only a little so that a catching of the casters with the blood treatment device is avoided as much as possible. The casters or wheels of the mobile apparatus are preferably designed in accordance with DE 19 39 923 A1, to which reference is made in this respect. Accordingly, the casters or wheels comprise a rotatably arranged hub body which has a plurality of rotatable casters which project on its periphery beyond the hub body periphery and whose axes of rotation extend in the direction of the tangents at the hub body periphery. It is possible by this design also to move the mobile apparatus easily in directions perpendicular to one another in the loaded state.

Reference is made with respect to further conceivable embodiments of the casters or wheels to DE 19 39 923 A1, which is in this respect included in the disclosure content of the present invention.

The tank can be made as a rigid vessel or also as at least partly flexible bags.

Provision is preferably made that the tank is made as a disposable article. The tank, which can be made as a bag, is replaced for each new filling in a preferred embodiment of the invention. The cleaning between the fillings can thereby be dispensed with.

It is advantageous if the mobile apparatus is made such that it mechanically supports the tank, in particular the bag. This has the advantage that the tank or the bag itself has to have a lower strength than if a mechanical support by the mobile apparatus were not present. Provision is made in a further preferred embodiment of the invention that the apparatus is made gas tight. This means that the apparatus itself serves as a gas barrier to prevent the loss of $CO_2$. This embodiment of the invention allows the use of a comparatively inexpensive material of the tank (which can be made as a bag, for example) since correspondingly lower demands are to be made on its gas barrier properties.

Provision is made in a further embodiment of the invention that the tank is made as a multi-chamber tank, in particular as a multi-chamber bag, of which at least one chamber serves the reception of treatment fluid and of which at least one chamber serves the reception of consumed treatment fluid and/or that the mobile apparatus has means for the leading off of consumed treatment fluid into an outflow or into another reception unit.

If the tank is provided as the multi-chamber bag, this brings along the advantage that the bag volume overall is not subject to changes or is only subject to insignificant changes during the treatment. It is conceivable that the volume of dialysis fluid which is supplied to the treatment device is replaced by the volume of consumed dialysis fluid and optionally additionally by ultrafiltrate.

A further advantage comprises the internal heat recovery: the used dialysate outputs heat to the fresh dialysate, which results in a reduced heating requirement. If the tank or bag for the used dialysate surrounds the tank or bag for the fresh dialysate (bag-in-bag concept), good heat insulation for the fresh dialysate results as a further advantage.

Alternatively to such a procedure, it is naturally also possible to use a further tank or bag in which consumed dialysis fluid and optionally ultrafiltrate is received. It is finally also possible to provide a direct outflow line through which consumed treatment fluid and optionally ultrafiltrate is led into an outflow or into another reception unit by means of the mobile apparatus.

Provision is made in a further embodiment of the invention that the system furthermore has at least one filling unit by means of which the tank of the mobile apparatus can be filled with treatment fluid.

The filling unit can have means by means of which it establishes the treatment fluid from a plurality of components, preferably from one or more concentrates and water.

It is also conceivable that the filling unit also only provides water in a suitable quality (purity, temperature and quantity). Provision can be made in this respect that the concentrate is already present in the tank or bag.

The filling unit can furthermore have means for the emptying of the used solution.

For this purpose, the filling unit can be in connection with an RO water supply unit or have such a unit.

As stated above, it is conceivable that the mobile apparatus is connected in a suitable manner to the blood treatment device. It must be taken into account in this respect that a rolling away of the mobile apparatus from its station position is prevented. It is conceivable to connect or latch the mobile apparatus to a guide element, for example, to a guide tongue of the blood treatment device, when the mobile apparatus is in its final position. This guide element or the guide tongue furthermore provides a good possibility to introduce the comparatively heavy, filled apparatus into the blood treatment device without the mobile apparatus and the blood treatment device being able to get caught on the pushing in. Such a guide can be arranged at the mobile apparatus and/or at the blood treatment device.

To enable the latching and release of the mobile apparatus with a small force effort, a ball can be provided which is attached, for example, to the lower side of the mobile apparatus and which can engage into a cut-out of the blood treatment device, for example of the guide tongue.

The present invention furthermore relates to a method for the supply of a blood treatment device, in particular of a dialyzer, with a treatment fluid, in particular having a dialysis fluid, which is removed from a tank during the carrying out of a blood treatment. The method is characterized in that the tank is an element of a mobile apparatus which is connected to the blood treatment device for the carrying out of the blood treatment such that a fluid connection is present between the tank and the blood treatment device.

The term "tank" is to be understood in a wide sense and also includes, for example, proprietary medicinal products, such as HF solutions.

The method can furthermore include the step that consumed treatment fluid, in particular consumed dialysis fluid, is supplied to the tank or to a tank of the mobile apparatus or is supplied to an outflow or to another reception unit by means of the mobile apparatus.

Provision is made in another embodiment of the invention that the mobile apparatus is first moved to a filling unit in which the tank of the mobile apparatus is filled with treatment fluid, in particular with fresh dialysis fluid.

The method can be carried out such that treatment fluid is removed from the at least one tank and used treatment fluid is supplied to the at least one tank simultaneously or offset in time. The case is generally also covered by the invention that different tanks or bags are used which store the fresh treatment fluid, on the one hand, and receive the consumed treatment fluid, on the other hand.

The method can furthermore include the step that, after the movement of the mobile apparatus to the blood treatment device into a preset position, at least one fluid connection is established automatically or on demand between the tank and the blood treatment device. The same can also apply accordingly to a data connection which serves to transfer data from the mobile apparatus to the blood treatment device and/or vice versa.

The mobile apparatus can be moved to the filling unit and used treatment fluid, in particular used dialysis fluid, can be supplied to the filling unit from the tank of the mobile apparatus. It is thus conceivable that the filling unit not only serves for the filling of the tank of the mobile apparatus with treatment fluid, but rather also to remove used treatment fluid from the tank of the mobile apparatus. Separate fluid circuits are particularly advantageous for hygienic reasons. A separate emptying unit can also be used.

The present invention furthermore relates to a blood treatment device, in particular to a dialyzer having means for the carrying out of a blood treatment, preferably of an external blood treatment and in particular a dialysis treatment. The device is characterized in that it does not have any tank in which a treatment fluid, in particular a dialysis fluid, required to carry out the blood treatment is present. Provision is rather made that the blood treatment device has at least one connection by means of which the blood treatment device can be connected to at least one tank in which the treatment fluid is present and through which the treatment fluid can be supplied to the blood treatment device during the blood treatment.

The blood treatment device can have at least one mount into which a mobile apparatus, preferably a mobile apparatus in accordance with the invention, can be received which has the at least one tank.

The present invention finally relates to the use of a mobile apparatus having at least one tank in which a treatment fluid, in particular a dialysis fluid, is located for the supply of a blood treatment device, in particular a dialyzer, with the treatment fluid during a blood treatment carried out by the blood treatment device. The mobile apparatus is preferably made in accordance with one or more of the aforesaid features and/or of the features described in the following.

BRIEF DESCRIPTION OF THE DRAWINGS

Further details and advantages of the invention will be explained in more detail with reference to an embodiment shown in the drawing. There are shown:

FIG. 1 shows a system for carrying out a blood treatment in accordance with the present invention. It comprises the actual blood treatment device 100 having means for external blood treatment, the mobile apparatus 200 and the filling unit 300.

Figure 1:
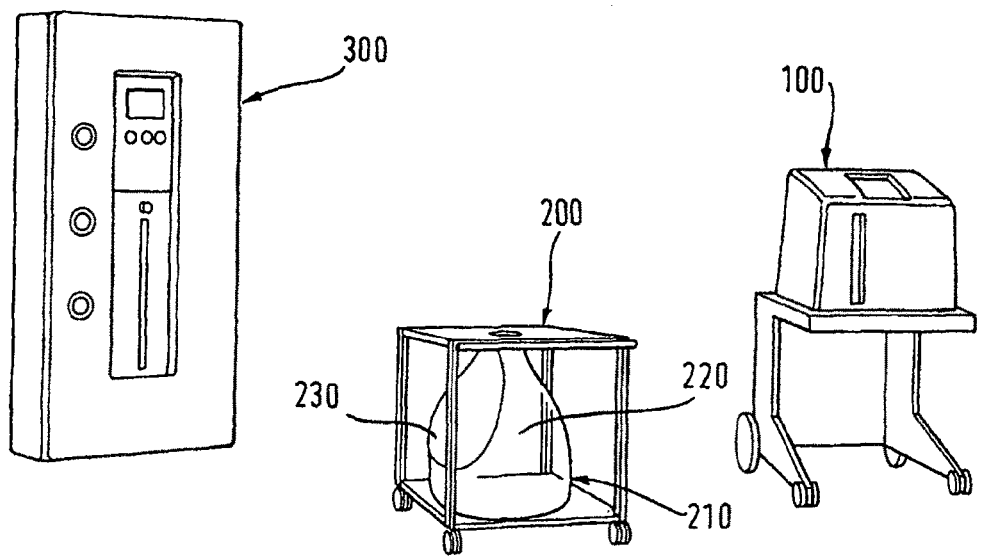
FIG. 1: a schematic representation of a system in accordance with the invention with a dialyzer, a mobile apparatus and a filling unit.

The system preferably serves the extracorporeal blood treatment, in particular for hemodialysis, home hemodialysis (HHD) and the treatment of acute renal failure. Other applications can also be peritoneal dialysis, in particular APD. The present system can be used for discontinuous processes (iHD and EDD) as well as for continuous applications (for example CWHD and CWH).

The mobile apparatus 200 has a tank, in the form of a twin-chamber bag 210 (or in the form of two separate bags), whose one chamber is filled with fresh dialysis fluid 220, which is in turn manufactured with the aid of the filling unit 300 and which is filled into the twin-chamber bag 210. In the embodiment shown here, the dialysis fluid is thus provided in the form of a batch.

The case is, however, also covered by the invention that dialysis fluids, which are present, for example, in bags or other reception containers, can be utilized and can be moved to the blood treatment device 100 using a mobile apparatus. It can in particular also be a case of HF solutions in this respect, for example.

The batch of dialysis fluid is manufactured locally by the preferably stationary filling unit 300 by the dilution of concentrates with purified water, preferably with RO water. The filling unit 300 can be a small unit which can, for example, be fixed to a wall or is otherwise stationary or also movable. It can have a separate RO unit or can be connected thereto or it can also contain an integrated RO unit. Further water treatment units can also be arranged in the filling unit. They include, for example, means for the supply of disinfectants which are optionally used for the disinfection of components or of the water used for the manufacture of the dialysis fluid. It is further advantageous that the filling unit has heating means with which the water or the manufactured dialysis fluid can be heated.

Liquid concentrates or also solid concentrates, which are then mixed with water to manufacture the dialysis fluid, can be used for the manufacture of the dialysis fluid.

Connections with minimal (reduced) contamination risk are preferably used in the filling unit 300 to ensure that the manufacture of the dialysis fluid takes place under conditions with a low microbiological count.

After the manufacture of the dialysis fluid 220, it is filled into the tank 210 or into a chamber of the twin-chamber bag 210 of the mobile apparatus 200. This process is shown schematically in FIG. 2 and is marked by the reference symbol A. The bag 210 is arranged in the mobile apparatus 200 for transport purposes. The size of the bag or of the tank 210 can lie, for example, in the range of 15 l to 120 l, preferably in the range from 40 l to 80 l.

The bag 210 of the mobile apparatus 200 can preferably be flexible and the two chambers of the twin-chamber bag 210 are in communication with one another such that the volume increase of one chamber can result in a corresponding volume reduction of the other chamber, as will be shown in more detail below.

After the filling of the tank 210 of the mobile apparatus 200, the latter is moved to the blood treatment device 100 (Step B), for which purpose the mobile apparatus 200 is made with casters.

The blood treatment device 100 can include a control unit which recognizes when the mobile apparatus 200 has reached its predefined position (this can, for example, be the end position or also intermediate positions) in the blood treatment device 100. The blood treatment device 100 furthermore includes a user interface by means of which operating states of the blood treatment device 100 or of the mobile apparatus 200 can be displayed to the user and by means of which the user can optionally make inputs. The blood treatment device 100 furthermore has means for the carrying out of an extracorporeal blood treatment, in particular means for the carrying out of a dialysis treatment such as a hose kit (cassette system/integrated disposable article), a blood pump, a dialysis pump, a dialysis machine with corresponding hose lines, etc.

Once the mobile apparatus 200 has reached its designated position in the blood treatment device 100 or is integrated therein, a fluid connection is established automatically or on demand by the user between the tank 210 of the mobile apparatus 200 and the blood treatment device 100. This fluid connection is made so that fresh treatment fluid 220 is supplied from a part of the twin-chamber bag 210 to the blood treatment device 100 while the dialysis is ongoing. A further fluid connection is made so that used dialysis fluid 230 arising during the dialysis treatment is filled into the other chamber of the twin-chamber bag 210. In addition, ultrafiltrate can be led off into this chamber or also into a further chamber. The blood treatment device comprises the actual treatment device 105 beneath which a receiving space 106 is arranged for the reception of the mobile device.

Figure 2:
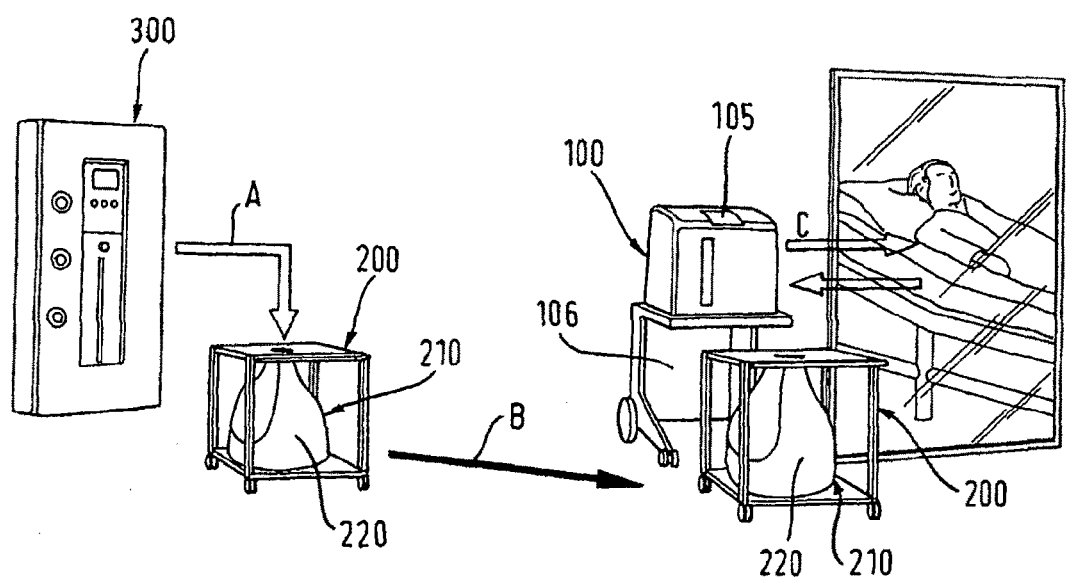
FIG. 2: a schematic view of the filling of the tank of the mobile apparatus by the filling unit and of the coupling of the mobile apparatus to the blood treatment device.
Figure 3:
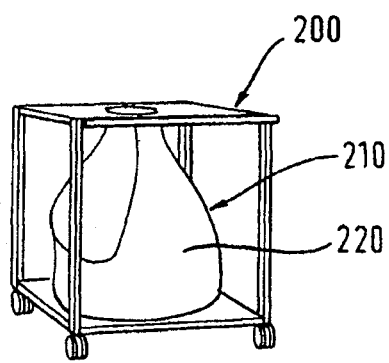
FIG. 3: a schematic view of the mobile apparatus with a two-chamber bag, with the chamber being filled for the reception of the non-consumed dialysis fluid.

FIG. 2 shows the process of the coupling of the mobile apparatus 200 to the blood treatment device 100. The extracorporeal blood circuit in accordance with Step C, via which the patient is connected to the blood treatment device 100, is symbolized by the double arrows in FIG. 3.

The mobile apparatus 200 can be replaced as required during the dialysis treatment or the blood treatment without the patient having to be disconnected from the extracorporeal blood circuit. The mobile apparatus 200 can be replaced by a mobile apparatus 200 which has a tank 210 filled with fresh treatment fluid 220.

Figure 4:
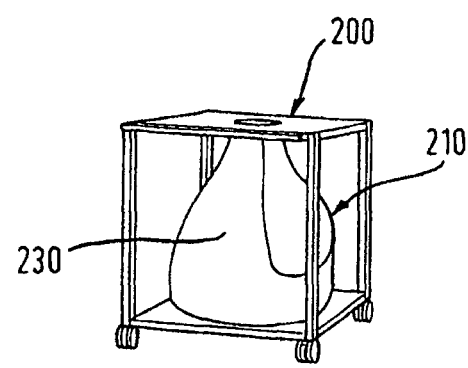
FIG. 4: a schematic view of the mobile apparatus with a two-chamber bag, with the chamber being filled for the reception of the consumed dialysis fluid.

FIG. 4 shows the tank 210 of the mobile apparatus 200 in a state in which the chamber for the reception of the consumed treatment fluid 230 is empty and the chamber is filled for the reception of the fresh dialysis fluid 220. The volume of the chamber in which the fresh dialysis fluid 220 is present falls during the blood treatment. At the same time, the volume of the chamber which serves the reception of the consumed dialysis fluid and optionally of ultrafiltrate increases due to the return of consumed dialysis fluid.

FIG. 4 shows the twin-chamber bag 210 of the mobile apparatus 200 in a state after the treatment. It can be seen here that the chamber of the twin-chamber bag 210 which serves the reception of the consumed dialysis fluid 230 and optionally of ultrafiltrate is now filled.

If no ultrafiltrate is removed, the volume of the bag 210 does not change or hardly changes during the process since consumed dialysis fluid 230 is supplied to the same degree as fresh dialysis fluid 220 is removed.

Other embodiments of the tank 210 are naturally also covered by the invention. The tank can be made as rigid, for example. The case is also covered by the invention that mutually separate bags or other vessels, that is, bags or other vessels not in communication with one another, are used for the non-consumed dialysis fluid 220, on the one hand, and for the used dialysis fluid 230, on the other hand.

Once the dialysis fluid has been used, the mobile apparatus 200 is decoupled from the blood treatment device 100 and moved to the filling unit 300. Here, the consumed dialysis fluid 230 and, optionally ultrafiltrate, is removed from the bag 210 by pumping and then the tank or bag 210 used as a disposable article is disposed of.

The mobile apparatus 200 can then be used with a new tank or bag 210 and is then again available for filling.

Figure 5:
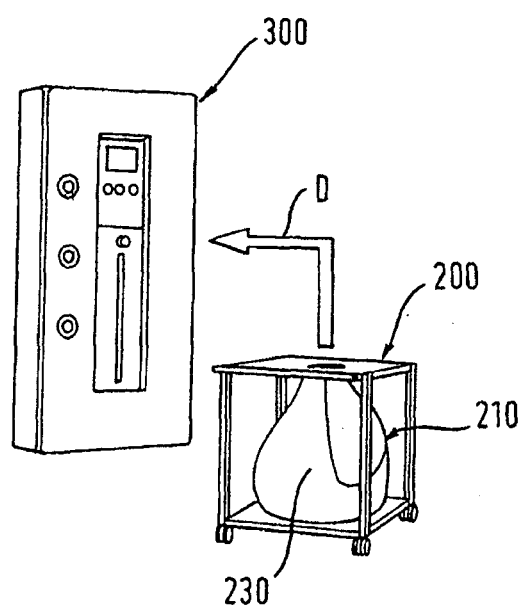
FIG. 5: a schematic view of the filling unit with the mobile apparatus, with the filling unit also serving as a unit for the emptying of the tank of the mobile apparatus.

The process of emptying the bag 210 of the mobile apparatus 200 by the filling unit 300 is shown in FIG. 5 (Step D).

The emptying takes place, for example, by a pump of the filling unit 300 which in this case also serves as an emptying unit. It is generally likewise conceivable to use different units or a separate (single) pump for the filling and emptying.

The blood treatment device 100 can be made with control means such that its operation is particularly simple. It is thus conceivable, for example, that it is automatically recognized when a mobile apparatus 200 is introduced into the blood treatment device 100. A connection with the tank 210 or with the bag 210 of the mobile apparatus 200 can then take place automatically. Furthermore, a data connection can take place such that data from the mobile apparatus 200 are read out by the blood treatment device 100. These data can, for example, relate to the dialysis fluid 220 (quantity, composition) in the bag 210.

It is conceivable to display the successful connection to the user and for him to start the dialysis treatment by actuation of a further keypad or of a switch or the like.

Provision can equally be made that the blood treatment device 100 indicates to the user when the dialysis treatment is ended or when the reception capacity of the bag 210 for consumed dialysis fluid 230 is exhausted.

In this case, it can, for example, be acoustically and/or optically indicated to the user that the mobile apparatus 200 has to be disconnected from the blood treatment device 100.

In the embodiment shown here, the blood treatment device 100 has means for the carrying out of the extracorporeal blood treatment. The only exception is a tank for the reception of fresh dialysis fluid 220. Such a tank is not provided in the blood treatment device 100, but is rather, as stated above, provided by a mobile apparatus 200 which can be moved to the blood treatment device 100 to be able to start the dialysis.

The advantages of the system can be summarized as follows in a preferred embodiment of the invention:

Batch change while the patient remains connected;
No bag change (5 l bags/waste bag);
Reduced labor effort (waste disposal with mobile unit);
Hygiene: closed system, reduced risk of contamination;
fluid system based on disposable articles (no fixed hydraulics in the mobile system/treatment unit, reduced disinfection effort);
Integrated alarm management (information transfer).

The invention claimed is:

1. A system for the carrying out of a blood dialysis, the system comprising as separate components
   a) at least one blood dialyzer (100) having no tank from which dialysis fluid (220) is removed during the blood dialysis and into which consumed dialysis fluid (230) is filled during the blood dialysis,
   b) at least one multi-chamber bag (210) having flexible walls, at least one first chamber serving the reception of dialysis fluid (220), and at least one second chamber serving the reception of consumed dialysis fluid (230), wherein the first and second chambers are in communication with one another such that a volume increase of one chamber results in a corresponding volume reduction in the other chamber, from which bag dialysis fluid (220) is removed during the carrying out of the blood dialysis, and into which consumed dialysis fluid (230) is filled during the carrying out of the blood dialysis, wherein the multi-chamber bag is mechanically supported by a mobile apparatus (200) which is to be releasably connected to the blood dialyzer (100) such that at least one fluid connection is to be established between the bag (210) and the blood dialyzer (100) and a data connection is established such that data from the mobile apparatus relating to dialysis fluid in the bag are read out by the dialyzer, and c) at least one stationary filling unit (300) which is adapted to be releasably connected to the bag to fill the bag with dialysis fluid, wherein the mobile apparatus is adapted for moving between, when not connected to either of, the blood dialyzer and the filling unit.

2. A system in accordance with claim 1, further comprising at least one fluid connection between the bag (210) and the blood dialyzer (100) provided automatically or on demand after the moving of the mobile apparatus (200) into and the blood dialyzer (100) into a predefined positions.

3. A system in accordance with claim 1, characterized in that the blood dialyzer (100) has a mount for reception of the mobile apparatus (200).

4. A system in accordance with claim 1, characterized in that the mobile apparatus (200) has casters providing easy movability.

5. A system in accordance with claim 1, characterized in that the mobile apparatus (200) is gas-tight.

6. A system in accordance with claim 1, characterized in that the mobile apparatus (200) has means for the leading off consumed dialysis fluid (230) from the bag into an outflow or into another reception unit.

7. A system in accordance with claim 1, characterized in that the filling unit (300) has means by means of which the dialysis fluid (220) is to be manufactured from one or more concentrates and water.

8. A system in accordance with claim 1, characterized in that the filling unit (300) is in communication with an RO water supply unit or has such a unit.

9. A method comprising the steps of supplying a blood dialyzer (100) with a dialysis fluid (220) which is removed from a multi-chamber bag (210) during carrying out of a blood dialysis, characterized in that the multi-chamber bag has flexible walls, at least one first chamber serving the reception of dialysis fluid (220), and at least one second chamber serving the reception of consumed dialysis fluid (230), wherein the first and second chambers are in communication with one another such that a volume increase of one chamber results in a corresponding volume reduction in the other chamber, wherein the bag is mechanically supported by a mobile apparatus (200) which is connected to the blood dialyzer (100) for the carrying out of the blood dialysis such that a fluid connection is present between the bag (210) and the blood dialyzer (100) and a data connection is established such that data from the mobile apparatus relating to dialysis fluid in the bag are read out by the dialyzer, and, after carrying out the blood dialysis, releasably connecting the mobile apparatus to a filling unit, to establish a fluid connection between the bag and the filling unit, and supplying the bag with blood dialysis fluid from the filling unit (300).

10. A method in accordance with claim 9, further comprising the step of supplying consumed dialysis fluid (230) to the bag (210) from the blood dialyzer through the fluid connection.

11. A method in accordance with claim 9, further comprising the steps of moving the mobile apparatus (200) to the filling unit (300) followed by filling the bag (210) with dialysis fluid (220) from the filling unit.

12. A method in accordance with claim 10, characterized in that the method is carried out such that dialysis fluid (220) is supplied from the at least one bag (210) and consumed dialysis fluid (230) is supplied to the at least one bag (210) simultaneously or offset in time.

13. A method in accordance with claim 11, characterized in that, after the movement of the mobile apparatus (200) to the blood dialyzer (100) into a preset position, at least one fluid connection is established automatically or on demand between the bag (210) and the blood dialyzer (100).

14. A method in accordance with claim 11, characterized in that, after the movement of the mobile apparatus (200) to the blood dialyzer (100) into a preset position, the data connection is established automatically or on demand between the mobile apparatus (200) and the blood dialyzer (100).

15. A method in accordance with claim 11, characterized in that the mobile apparatus (200) is moved to the filling unit (300) or to a separate emptying unit and consumed dialysis fluid (230) is disposed of from the bag (210) by the filling unit (300) or by the separate emptying unit.

\* \* \* \* \*